United States Patent
Sumner et al.

(10) Patent No.: US 7,045,669 B2
(45) Date of Patent: May 16, 2006

(54) DUAL PRESSURE CATALYTIC DISTILLATION HYDROGENATION COLUMN SYSTEM FOR THE FRONT END OF AN ETHYLENE PLANT

(75) Inventors: Charles Sumner, Livingston, NJ (US); Jeffrey L. Heineman, Madison, NJ (US); Christopher A. Di Biase, Wharton, NJ (US)

(73) Assignee: Catalytic Distillation Technologies, Pasadena, TX (US)

( * ) Notice: Subject to any disclaimer, the term of this patent is extended or adjusted under 35 U.S.C. 154(b) by 458 days.

(21) Appl. No.: 10/635,763

(22) Filed: Aug. 5, 2003

(65) Prior Publication Data

US 2005/0033098 A1    Feb. 10, 2005

(51) Int. Cl.
*C07C 5/00*     (2006.01)

(52) U.S. Cl. ............... 585/259; 585/260; 585/265; 585/809; 203/DIG. 6

(58) Field of Classification Search ............ 585/259, 585/260, 265, 264, 809; 202/DIG. 6
See application file for complete search history.

(56) References Cited

U.S. PATENT DOCUMENTS

| | | | |
|---|---|---|---|
| 4,215,011 A | 7/1980 | Smith | 252/426 |
| 5,189,001 A | 2/1993 | Johnson | 502/159 |
| 5,679,241 A | 10/1997 | Stanley et al. | 208/92 |
| 5,730,843 A | 3/1998 | Groten et al. | 202/158 |
| 6,000,685 A | 12/1999 | Groten et al. | 261/112.2 |
| 6,759,562 B1 | 7/2004 | Gartside et al. | 585/265 |

FOREIGN PATENT DOCUMENTS

WO    WO95/15934    6/1995

*Primary Examiner*—Tam M. Nguyen
(74) *Attorney, Agent, or Firm*—Kenneth H. Johnson

(57) ABSTRACT

The charge gas from the thermal cracking of a hydrocarbon feedstock is processed in a front-end catalytic distillation hydrogenation system of an olefins plant to more effectively recover ethylene and propylene product and to process the by-products. The rate of fouling in the system is reduced by employing two columns in the system with the first column operating at a higher pressure and the second column operating at a lower pressure. The hydrogenation as well as fractionation takes place in the first column while the second column is only a fractionator. The temperature of the bottoms from each column is maintained at a temperature less than 200° C. to avoid fouling.

21 Claims, 4 Drawing Sheets

US 7,045,669 B2

DUAL PRESSURE CATALYTIC DISTILLATION HYDROGENATION COLUMN SYSTEM FOR THE FRONT END OF AN ETHYLENE PLANT

BACKGROUND OF THE INVENTION

The present invention relates to a process and system for the production of olefins and particularly to processing the charge gas feed to more effectively recover the product and process the by-products.

Ethylene, propylene and other valuable petrochemicals are produced by the thermal cracking of a variety of hydrocarbon feedstocks ranging from ethane to vacuum gas oils. In the thermal cracking of these feedstocks, a wide variety of products are produced ranging from hydrogen to pyrolysis fuel oil. The effluent from the cracking step, commonly called charge gas or cracked gas, is made up of this full range of materials which must then be separated (fractionated) into various product and by-product streams followed by reaction (hydrogenation) of at least some of the unsaturated by-products.

The typical charge gas stream, in addition to the desired products of ethylene and propylene, contains $C_2$ acetylenes, $C_3$ acetylenes and dienes and $C_4$ and heavier acetylenes, dienes and olefins as well as a significant quantity of hydrogen and methane. Aromatic as well as other ring compounds and saturated hydrocarbons are also present.

In U.S. Pat. No. 5,679,241 and U.S. patent application Ser. No. 10/202,702, filed Jul. 24, 2002, ethylene plant front-end catalytic distillation column systems are disclosed in which the highly unsaturated hydrocarbons, as acetylenes and dienes, are reacted with the contained hydrogen in the steam cracker charge gas compressor train to form olefins. In the process, it is desired to control the catalyst bed temperatures to as high a level as possible consistent with a low fouling rate. This maximum temperature minimizes the quantity of catalyst required. It can also increase overall selectivity to ethylene and propylene. The conditions that achieve the optimum catalytic distillation catalyst temperature can, however, result in a column bottoms temperature that is relatively high and can increase the fouling rate in the bottom of the column. While this fouling rate can be controlled by adding inhibitors, it is desirable to design the catalytic distillation hydrogenation system to achieve high catalyst bed temperatures while maintaining a low bottoms temperature and a low core fouling rate in the column system.

SUMMARY OF THE INVENTION

The object of the invention is to provide and operate a front-end catalytic distillation hydrogenation system in an olefins plant to maximize the catalyst bed temperatures in the system while maintaining a low bottoms product temperature to reduce the fouling rate. The invention involves using two columns operating at different pressures. The catalytic reactor structures are in the first, high pressure column together with some fractionation zones. In the bottoms of the high pressure column, the temperature is regulated such that some lighter hydrocarbons remain. The bottoms from the high pressure column is sent to a second column which is a fractionator, operating at a lower pressure. The net bottoms product of this column is the net bottoms from the system. The temperature of this stream is low because total pressure of the column is low. The catalyst bed temperatures remain about the same as a single column, single pressure system but the bottoms temperatures in each of the columns is significantly lower. The net overhead of the low pressure column is totally condensed and sent back to the high pressure column.

DESCRIPTION OF THE PREFERRED EMBODIMENTS

Figure 1:
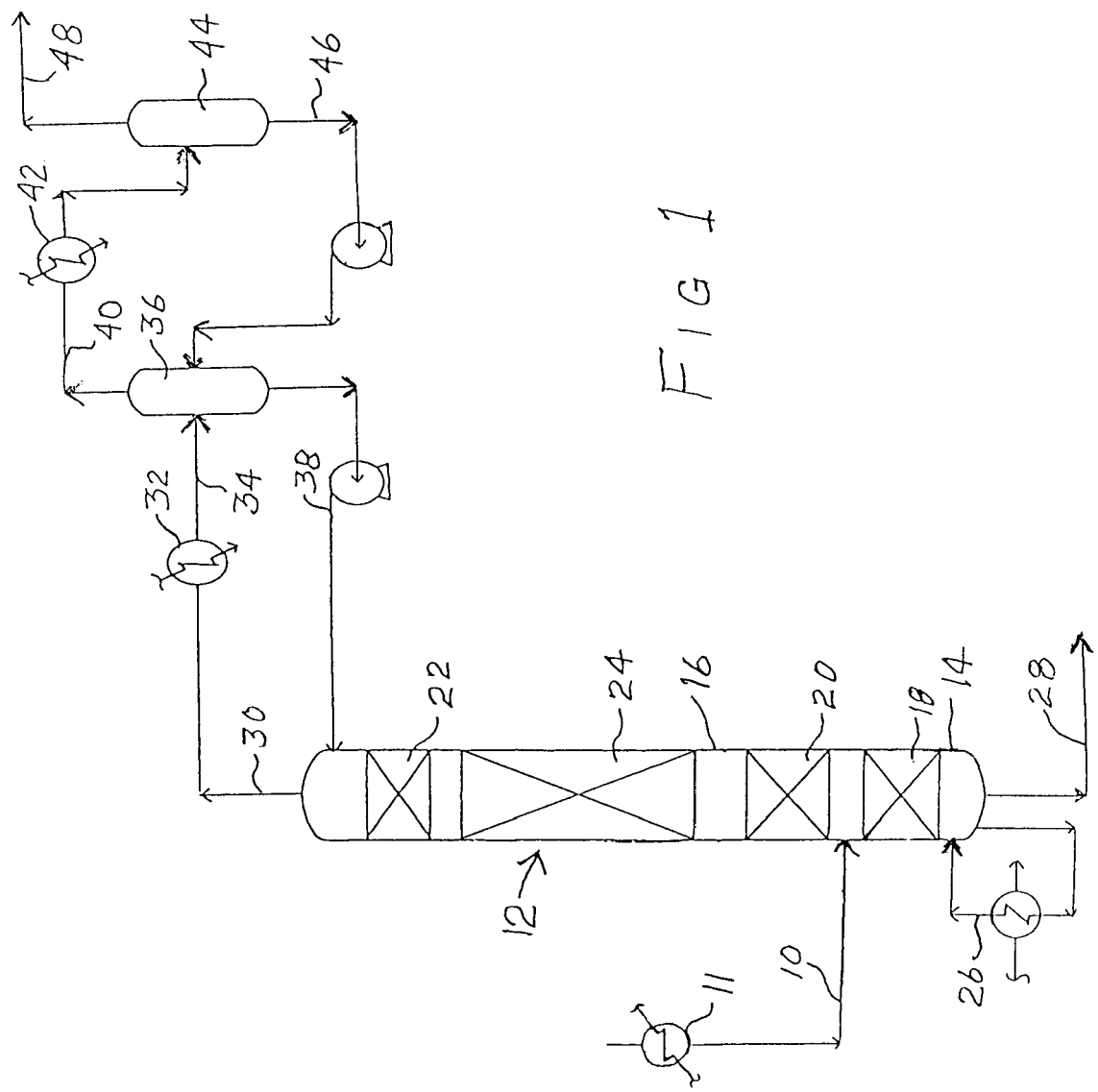
FIG. 1 is a flow sheet for a front-end catalytic distillation hydrogenation system according to the prior art.

For a better understanding of the present invention, a prior art front-end catalytic distillation hydrogenation system as represented by FIG. 1 will be briefly described. As previously mentioned, such systems are disclosed and much more fully described in U.S. Pat. No. 5,679,241 and U.S. patent application Ser. No. 10/202,702. The objective of these systems is to remove a significant fraction of the hydrogen by hydrogenating the $C_2$ to $C_5$ diolefins and acetylenes without significant hydrogenation of the ethylene and propylene. In this system, the compressed charge gas 10, which may be heated at 11, is fed to the catalytic distillation hydrogenation column 12 which simultaneously carries out a catalytic reaction and distillation. The column 12 has a stripping section 14 below the feed 10 and a rectifying/reaction section 16 above the feed. Both of the sections contain distillation internals forming separation zones 18, 20 and 22 while the rectifying/reaction section 16 contains one or more catalyst beds forming a catalyst zone 24. The column has a reboiler loop 26 and can also incorporate side condensers, interreboilers and pump-around either with or without heat exchange. None of these are shown but they are disclosed and shown in U.S. Pat. No. 5,679,241 and U.S. patent application Ser. No. 10/202,702 and can be utilized to enhance the performance of the dual pressure system in specific applications.

The bottoms liquid 28 when the column 12 is operated as a depentanizer contains the $C_6$ and heavier components and is usually used for gasoline processing. The column can also be operated as a debutanizer where the bottoms 28 is a $C_5+$ stream. The overhead vapor 30 from the column 12 passes through the condenser 32 and the partially condensed stream 34 is fed into the separation vessel 36. Cooling water is the preferred cooling medium in condenser 32. Vapor and liquid are separated and liquid reflux 38 is returned to the column 12. The vapor 40 is further cooled at 42 and fed to the separation vessel 44 with the liquid 46 being recycled back and combined with the reflux liquid in the vessel 36. The net vapor product 48 is then sent for further processing.

The prior art system of FIG. 1 is a single pressure system in which the entire catalytic distillation hydrogenation operation is carried out in a narrow pressure range. The following Table 1 is an example of a material balance of such a prior art system operated as a depentanizer and lists the key operating parameters involved. In this table and the following tables and throughout this description, the pressures are given as the absolute pressures. In order to maintain a desirable catalyst bed temperature of approximately 125° C. when operating the column system at a single operating pressure of approximately 17 kg/cm², with a feed gas obtained from cracking a typical naphtha at moderate cracking severity, it can be seen in Table 1 that the bottoms temperature is 203° C. At this temperature, it is possible that some fouling could occur without the use of inhibitors. If the system of FIG. 1 were operated as a debutanizer, the specific data would vary but the bottoms temperature would still be high. This is because the debutanizer must operate at a higher pressure than a depentanizer for the column 12 overhead to be partially condensed by ambient temperature cooling medium.

TABLE 1

| Stream No. | Stream 10 | Stream 48 | Stream 28 | Stream 38 |
|---|---|---|---|---|
| Name | Feed | Net Overhead | Bottoms | Reflux |
| Phase | Vapor | Vapor | Liquid | Liquid |
| Fluid mol % | | | | |
| Hydrogen | 16.8 | 12.9 | 0.0 | 0.4 |
| Methane | 27.8 | 29.6 | 0.0 | 2.1 |
| Acetylene | 0.5 | 0.1 | 0.0 | 0.0 |
| Ethylene | 30.2 | 32.3 | 0.0 | 9.1 |
| Ethane | 6.2 | 6.9 | 0.0 | 2.7 |
| MAPD | 0.5 | 0.2 | 0.0 | 0.4 |
| Propylene | 9.7 | 10.6 | 0.0 | 11.1 |
| Propane | 0.3 | 0.4 | 0.0 | 0.5 |
| Butadiene | 2.5 | 0.3 | 0.0 | 1.2 |
| Butene | 2.4 | 4.9 | 0.0 | 20.9 |
| Butane | 0.2 | 0.2 | 0.0 | 0.9 |
| Pentadiene | 1.0 | 0.0 | 0.0 | 0.6 |
| Pentene | 0.3 | 1.3 | 0.0 | 29.8 |
| Pentane | 0.1 | 0.2 | 0.0 | 5.9 |
| $C_6+$ | 1.5 | 0.1 | 100.0 | 14.4 |
| Total Rate, kg-mol/hr | 763 | 718 | 10 | 543 |
| Total Rate, kg/hr | 18787 | 17977 | 810 | 31965 |
| Molecular Weight | 24.6 | 25.0 | 81.0 | 58.9 |
| Temperature, ° C. | 41 | 16 | 203 | 38 |
| Pressure, kg/cm² | 17.6 | 16.2 | 17.7 | 16.7 |

Figure 2:
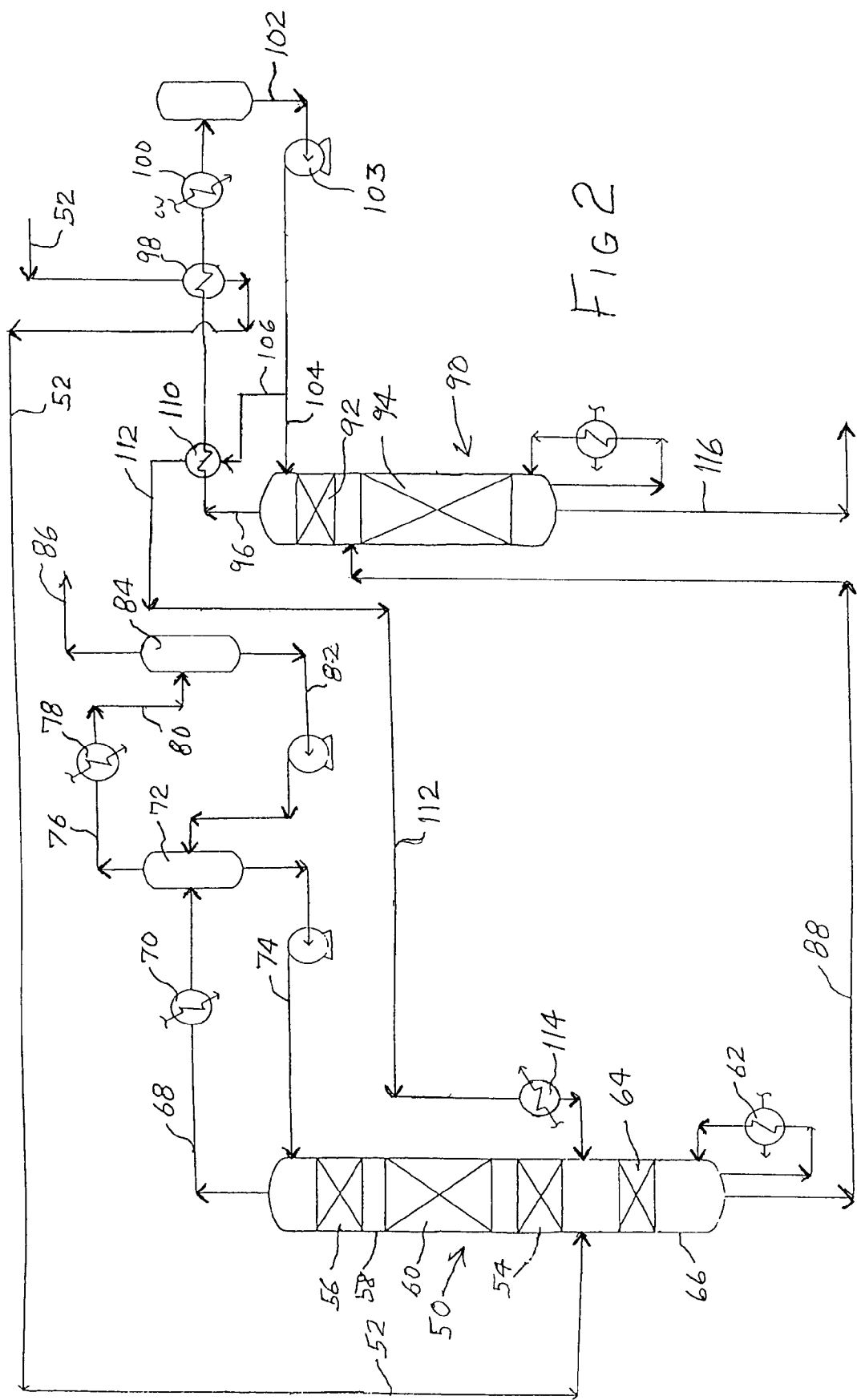
FIG. 2 is a flow sheet for a front-end catalytic distillation hydrogenation system according to the present invention illustrating two variations in the flow scheme.

The dual pressure catalytic distillation hydrogenation system of the present invention is shown in FIG. 2. The first column of this system is a high pressure column 50 which is operated generally at the same pressure as column 12 in FIG. 1 which, in this example, is in a narrow range of around 17 kg/cm² pressure. The high pressure column pressure can range from 14 to 20 kg/cm² depending on the composition of the cracked gas and the temperature of the cooling medium. A typical pressure is 16 to 18 kg/cm². The charge gas 52 from an intermediate or final stage of a charge gas compressor of an ethylene plant flows to this first, high pressure column 50 of the dual pressure column system. The charge gas feed 52 is preferably heated, although it can enter the high pressure column without preheating. Preferably, preheat temperatures range from 80 to 120° C. More preferably, the feed is preheated by heat exchange with the gross overhead of the low pressure column described later. Alternately, it can be preheated by the gross overhead of the high pressure column (not shown in FIG. 2), before cooling in the reflux condenser 70. The high pressure column 50 typically has two fractionation zones 54 and 56 in the rectifying/reaction section 58, one above and one below the catalyst zone 60. The catalyst zone 60 functions as a fractionation zone as well. Below the vapor charge gas feed 52 to the column 50, it is possible to utilize only the separation provided by the reboiler 62. Preferably, however, there is an additional fractionation zone 64 in this stripping section 66.

This fractionation zone 66, when present, typically consists of very few theoretical separation stages. The fractionation zones in both this high pressure column 50 and the low pressure column to be described use standard industrially-available mass transfer contacting devices, including trays, such as valve trays, sieve trays, segmental trays, shed decks, or packing such as random packing, structured packing, etc.

The charge gas feed 52 travels upwards in the high pressure column 50 and is contacted by downflowing liquid. The charge gas feed enters the catalytic distillation hydrogenation zone 60 wherein contained hydrogen in the gas reacts with unsaturates, especially acetylenes and dienes, to preferably form the corresponding olefin compounds. Any oligomerization products formed are washed off the catalyst by the downflowing hydrocarbon liquid. Thus, these compounds are removed from the catalyst surface immediately as formed, limiting the fouling rate over the catalyst. The catalyst zone 60 contains hydrogenation catalyst, such as noble metal catalysts or mixtures thereof, such as palladium or silver. Alternately, they can contain non-noble metal hydrogenation catalysts, such as nickel. Further alternately, they can contain both non-noble and noble metal catalysts, either admixed or preferably layered. The catalyst bed temperature is in the range of 90 to 135° C. and is 125° C. in this example.

The catalyst in the catalytic hydrogenation zone can be bulk-loaded, made up of extrudates, pellets, balls, open ring-shapes, etc. More preferably, the catalyst is part of a structure, such as catalyst deposited on the surface of wire mesh or other types of gauzes or catalyst contained on the walls of a monolith structure. Most preferably, the catalyst is contained in specially-designed containers, as described in U.S. Pat. Nos. 6,000,685, 5,730,843, 5,189,001, and 4,215,011.

Exiting the catalyst bed, the upflowing gas, with the bulk of the acetylenes and dienes hydrogenated, enters the second fractionation zone 56, where it is contacted with reflux. The overhead vapor 68 is partially condensed in the reflux condenser 70 against ambient temperature cooling, preferably cooling water. Vapor and liquid are separated at 72 and liquid reflux 74 is returned to the high pressure column 50. The vapor 76 can be further cooled in the vent condenser 78. If practiced, liquid 82 is separated at 84 from the vent condenser effluent and this liquid 82 is combined with the liquid from the main reflux condenser 70 and returned to the high pressure column as the reflux 74. The net vapor product 86 is then further hydrogenated to remove any remaining concentration of acetylene (not shown). After this, the vapor product would flow either to the charge gas compressor or to the chilling train of the ethylene plant for separation of valuable hydrocarbons and hydrogen products from fuel products. The valuable hydrocarbons are subsequently processed to produce chemical-grade and/or polymer-grade ethylene and propylene products.

In the high pressure column 50, there is preferably a small fractionation zone 64 below the vapor feed 52. Liquid flowing downwards in the column below the vapor feed is stripped (stabilized) of most of the light, high vapor pressure components, such as ethane and lighter, by contact with upwardly flowing vapor from the reboiler 62. Most of the $C_3$'s are also stripped. However, complete depentanization is not accomplished. Significant levels of $C_4$'s and $C_5$'s are allowed to leave in the bottoms 88 to keep the temperature low. Typically, the reboiler is heated by condensing steam. Alternately, waste heat from the ethylene plant, as quench oil can be utilized as the heating medium. The bottoms product 88 from the high pressure column 50 is low in light components and high in more mid-range components, especially in $C_4$ and $C_5$ hydrocarbons in addition to the $C_6+$ hydrocarbons. It is desirable to remove the lights from this stream so as to be able to totally condense the overhead stream in the low pressure column without using refrigeration. The temperature of the bottoms 88 from the high pressure column is less than 200° C. and preferably less than 160° C.

The bottoms product 88 from the high pressure column 50 is sent to the low pressure column 90, preferably without cooling. The low pressure column 90 in this example is also a depentanizer, similar to the high pressure column 50, and is operated at a pressure of about 6 kg/cm². The pressure for this low pressure column can range from 4 to 10 kg/cm² depending on composition. A typical pressure is 4 to 8 kg/cm². This low pressure column 90 contains separation zones 92 and 94 above and below the feed 88 respectively. The low pressure column preferentially has a few fractionating trays represented by 92 above the feed tray. Alternately, column 90 can be operated as a stripping column with feed 88 entering on the top tray or alternately directed into line 96 overhead of column 90. The overhead product is $C_5$'s and lighter and the bottoms product is $C_6$'s and heavier. The gross overhead 96 is totally condensed partially by heat exchange at 98 with the charge gas feed and then in heat exchanger 100. Cooling water is the preferred coolant in heat exchanger 100. The totally condensed stream 102 is pumped at 103 and a portion 104 of the liquid stream is then returned as reflux. The reflux can be returned at the temperature leaving pump 103, as shown in FIG. 2. Alternately, the reflux can be preheated against the gross overhead stream 96 in a separate exchanger service, or as an additional exchanger service in 110, by using multi-pass platefin exchangers (not shown). The net overhead product liquid stream 106 from the column 90 is preheated at 110 with heat from the overhead 96 and then returned as stream 112 to the high pressure column 50. This stream 112 is preferably partially vaporized before being returned to the high pressure column. Further preheating is accomplished in heat exchanger 114 by an external heat stream such as steam or some waste heat stream. The column entry point for this return heated stream 112 is typically below the catalyst bed 60, for example, at the same entry point as the vapor feed 52 to the system. This further preheating in heat exchanger 114 will decrease the reboiler duty requirement in the high pressure column. As the return stream has a negligible concentration of potential oligomers, it is preferable to maximize the heat input to this stream as compared to heat inputted into the high pressure column reboiler.

The bottoms 116 of the low pressure column is the $C_6+$ hydrocarbon components. The $C_5$ content of this stream 116 is typically less than 1% and preferably less than 0.1%. The temperature of this bottoms stream 116 is also less than 200° C. and preferably less than 160° C. This material is typically combined with pyrolysis gasoline streams collected elsewhere in the ethylene plant and further hydrogenated to produce motor gasoline. Alternately, the stream can be further treated to recover aromatics, as benzene or toluene or xylenes. Table 2 is a material balance for a system of the present invention according to FIG. 2 being operated as a depentanizer. This table lists the key operating parameters involved.

TABLE 2

| Stream No. | Stream 52 | Stream 86 | Stream 116 | Stream 74 | Stream 112 | Stream 88 | Stream 96 | Stream 104 |
| --- | --- | --- | --- | --- | --- | --- | --- | --- |
| Name | Feed | HP Column Net Overhead | LP Column Bottoms | HP Column Reflux | LP Column Return to HP Column | HP Column Bottoms | LP Column Overhead | LP Column Reflux |
| Phase | Vapor | Vapor | Liquid | Liquid | Liquid | Liquid | Vapor | Liquid |
| Fluid mol % | | | | | | | | |
| Hydrogen | 16.8 | 12.9 | 0.0 | 0.4 | 0.0 | 0.0 | 0.0 | 0.0 |
| Methane | 27.8 | 29.6 | 0.0 | 2.1 | 0.1 | 0.1 | 0.1 | 0.1 |
| Acetylene | 0.5 | 0.1 | 0.0 | 0.0 | 0.0 | 0.0 | 0.0 | 0.0 |
| Ethylene | 30.2 | 32.3 | 0.0 | 9.1 | 1.6 | 1.5 | 1.6 | 1.6 |
| Ethane | 6.2 | 6.9 | 0.0 | 2.7 | 0.6 | 0.6 | 0.6 | 0.6 |
| MAPD | 0.5 | 0.2 | 0.0 | 0.4 | 0.1 | 0.1 | 0.1 | 0.1 |
| Propylene | 9.7 | 10.6 | 0.0 | 11.1 | 3.2 | 3.1 | 3.2 | 3.2 |
| Propane | 0.3 | 0.4 | 0.0 | 0.5 | 0.1 | 0.1 | 0.1 | 0.1 |
| Butadiene | 2.5 | 0.3 | 0.0 | 1.2 | 0.3 | 0.2 | 0.3 | 0.3 |
| Butene | 2.4 | 4.9 | 0.0 | 20.9 | 4.2 | 4.0 | 4.2 | 4.2 |
| Butane | 0.2 | 0.2 | 0.0 | 0.9 | 0.2 | 0.2 | 0.2 | 0.2 |
| Pentadiene | 1.0 | 0.0 | 0.0 | 0.6 | 0.1 | 0.1 | 0.1 | 0.1 |
| Pentene | 0.3 | 1.3 | 0.0 | 29.8 | 4.0 | 3.9 | 4.0 | 4.0 |
| Pentane | 0.1 | 0.2 | 0.0 | 5.9 | 0.8 | 0.7 | 0.8 | 0.8 |
| $C_6+$ | 1.5 | 0.1 | 100.0 | 14.4 | 84.7 | 85.4 | 84.7 | 84.7 |
| Total Rate, kg-mol/hr | 763 | 718 | 10 | 477 | 225 | 235 | 233 | 9 |
| Total Rate, kg/hr | 18787 | 17977 | 810 | 28035 | 17495 | 18305 | 18185 | 690 |
| Molecular Weight | 24.6 | 25.0 | 81.0 | 58.8 | 77.9 | 78.0 | 77.9 | 77.9 |
| Temperature, ° C. | 41 | 16 | 147 | 38 | 124 | 150 | 127 | 39 |
| Pressure, kg/cm² | 17.6 | 16.2 | 6.5 | 16.7 | 17.5 | 17.4 | 6.0 | 6.1 |

The above description describes the invention operating as a depentanizer but the invention can also be practiced as a debutanizer. The flow scheme is similar but with higher operating pressures. The pressure is higher both in the high pressure column, to allow for reflux to be produced, and in the low pressure column to allow for the overhead to be cooled and totally condensed by ambient temperature media, preferably cooling water. The higher operating pressure in the high pressure column, with respect to a depentanizer operation, maintains the catalyst bed temperature at the desirable temperature range of 100 to 135° C., preferably 110–125° C. The flow scheme for operation as a debutanizer is similar to that of FIG. 2 or FIG. 3. The high pressure column pressure will range from 28 to 43 kg/cm², depending upon the composition of the cracked gas and the temperature of the cooling medium. Typical pressure is 34 to 39 kg/cm². The pressure of the low pressure column varies between 5 to 14 kg/cm². Typical pressure is 11 to 12 kg/cm². When operated as a debutanizer, the $C_5$ content in stream 86 is typically less than 1% and preferably less than 0.1%. The $C_4$ content in stream 116 is typically less than 1% and preferably less than 0.1%.

Figure 3:
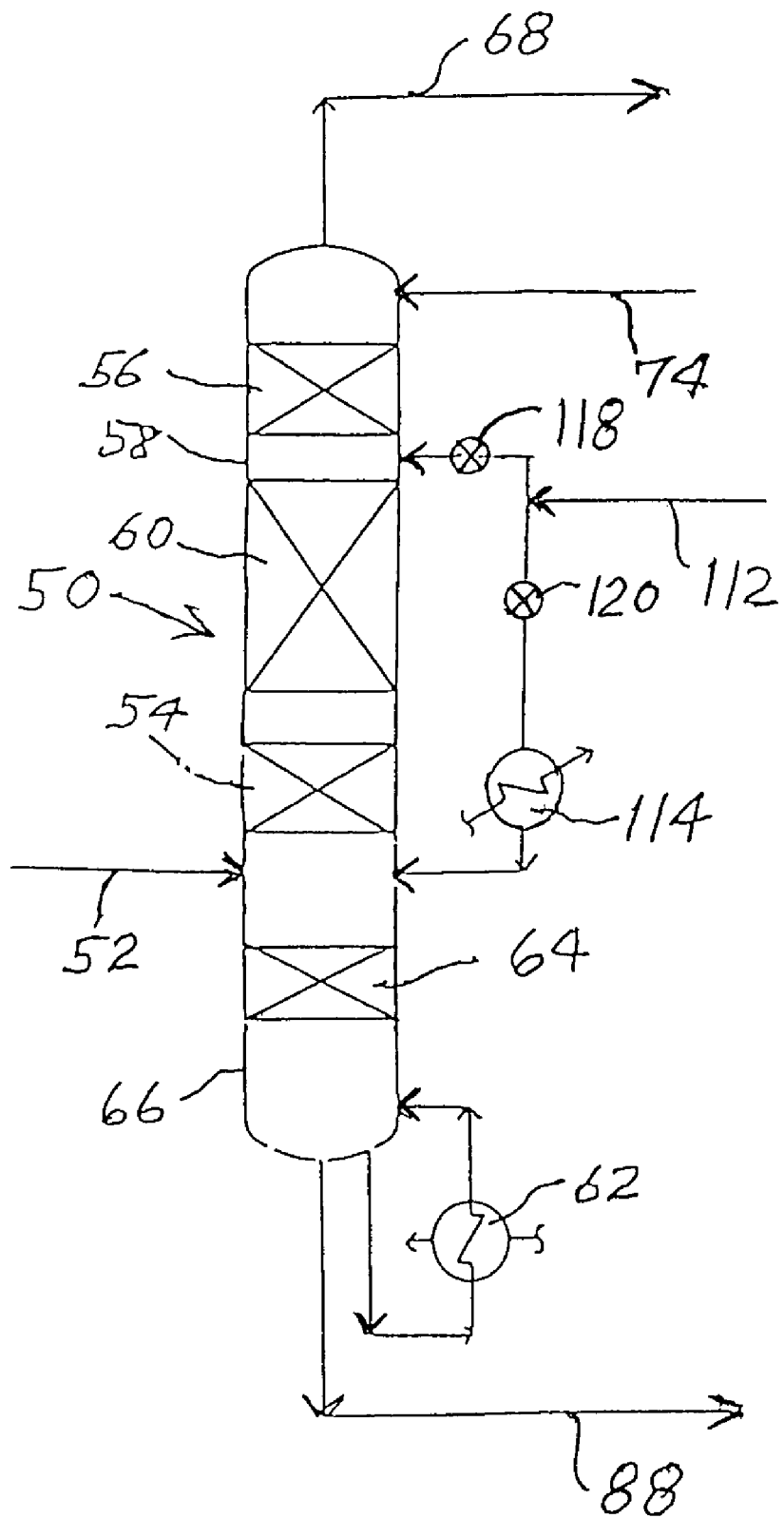
FIG. 3 illustrates a portion of the system of FIG. 2 but shows an alternate flow path for the return line from the low pressure column to the high pressure column.

A variation on the FIG. 2 flow scheme when operated as a depentanizer is shown in FIG. 3. In this variation, the net overhead 112 from the low pressure depentanizer 90 may be sent through valve 118 to the top of the high pressure depentanizer at a point above the catalyst bed 60. This is contrasted to FIG. 2 where this net overhead stream 112 is sent to the high pressure depentanizer below the catalyst bed. This alternate return point varies the liquid flow rate and composition over the catalyst bed, as compared to the FIG. 2 scheme, while achieving the same goal of reducing the maximum temperature in the system by approximately 50° C. The net column overhead from the low pressure column to the high pressure column can now be returned without preheating or with less preheating. Unlike the FIG. 2 flow scheme, the return stream for the FIG. 3 stream is not vaporized. It is also possible to send part of the net overhead from the low pressure depentanizer to the bottom of the high pressure depentanizer through valve 120 and the other part to the top of the catalyst bed. This provides additional flexibility in operation to vary catalyst bed conditions at the same overall maximum temperatures at the bottom of the two depentanizers.

The advantages of the present invention can be seen from a comparison of the key operating characteristics for the dual pressure system of the invention as shown in Table 2 versus a single pressure system of the prior art as shown in Table 1 where both are operating as depentanizers in front end catalytic distillation hydrogenation systems for a naphtha feedstock steam cracker.

Referring to Table 1, the operating pressures for the streams range from 16.2 to 17.7 kg/cm². The average catalyst bed temperature is maintained at approximately 125° C. and the highest temperature is stream 28, the net column bottoms, at 203° C.

Referring to Table 2, the high pressure column 50 of FIG. 2 is operated at the same pressure as the column 12 of FIG. 1. The feed 52 to the system and the net overhead 86 from the system are the same, in terms of flow rate, composition and temperature as in Table 1. Stream 116, which represents the net bottoms of the system, is the same in flow and composition as stream 28 in Table 1. However, in Table 2, the temperature of stream 116 is 147° C. versus the 203° C. temperature for stream 28 in Table 1. This lower temperature is because stream 116 in Table 2 is at 6.5 kg/cm² as compared to 17.7 kg/cm² in Table 1.

Stream 88 in Table 2 is the stream flowing from the first, high pressure depentanizer to the second, low pressure depentanizer. This stream pressure is 17.4 kg/cm² or approximately the same pressure as stream 28 in Table 1. However, this stream 88 temperature is 150° C. as compared to 203° C. for stream 28 of Table 1. This lower temperature is achieved by operating the high pressure depentanizer of FIG. 2 so that there is approximately 15 mol % of the $C_5$'s and lighter hydrocarbon in the stream 88, lowering the temperature of this stream. The average catalyst bed temperature is approximately 120° C. which is approximately the same average bed temperature of the prior art single pressure system configuration of FIG. 1. Thus, the FIG. 2 flow scheme, as demonstrated in the Table 2 data referring to this flow scheme achieves the purpose of maintaining catalyst bed temperatures but at the same time decreasing the maximum temperature in the system by approximately 50° C.

Figure 4:
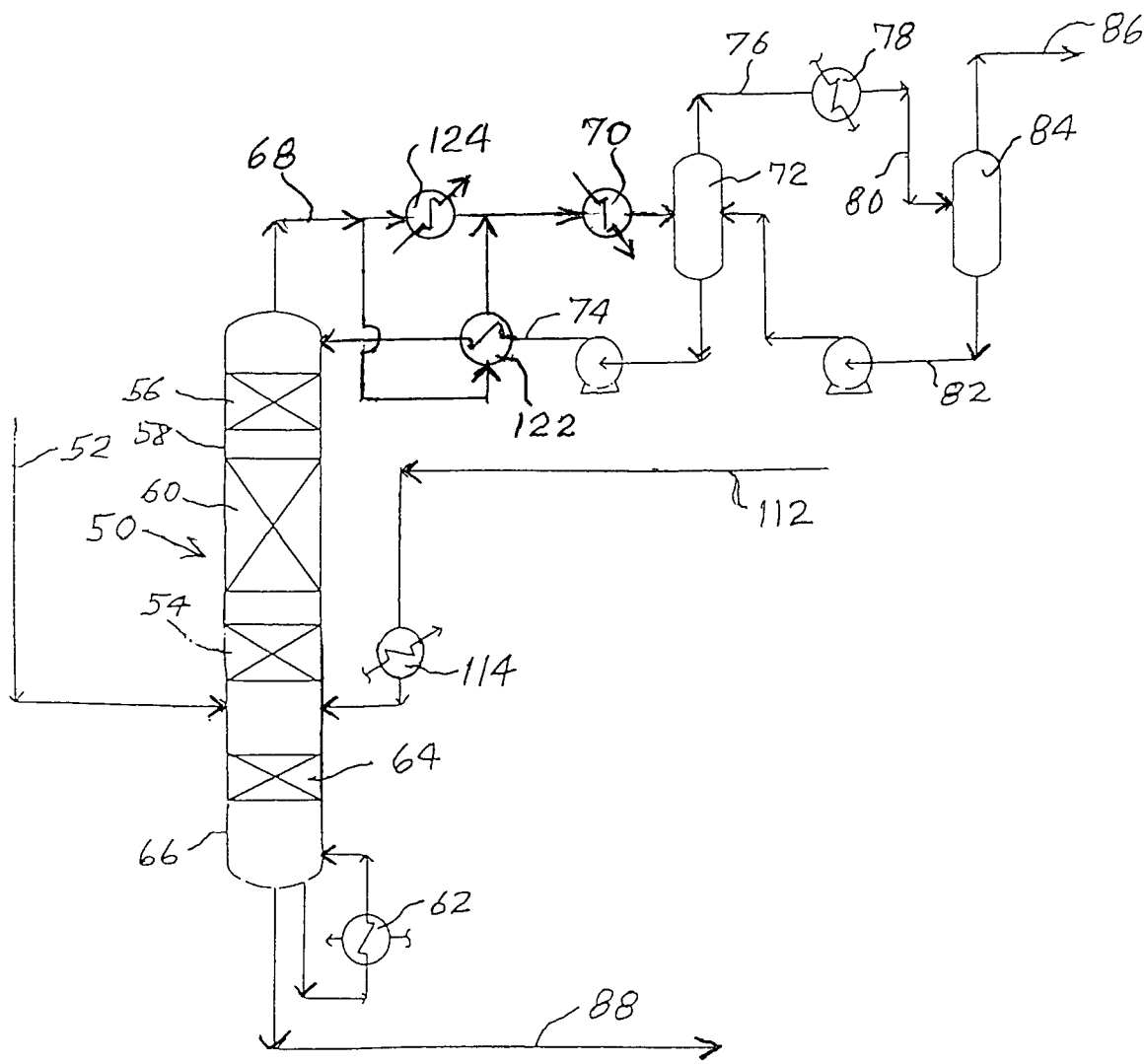
FIG. 4 also illustrates a portion of the system of FIG. 2 showing the addition of a heat recovery step in the overhead of the high pressure column.

FIG. 4 shows a variation of the FIG. 2 process scheme. In this variation, the pumped reflux stream 74 is preheated in heat exchanger 122 by cooling and partially condensing a portion of the overhead 68 of the high pressure column. This preheat results in a higher temperature of the vapor leaving the top tray of the column 50. All other process conditions in the column itself are essentially unchanged. The higher temperature leaving the column enables a greater degree of waste heat recovery as in exchanger 124. This waste heat can be utilized for preheating, as for preheating feed 52 (not shown in FIG. 4) or other services in the ethylene plant requiring low temperature heat. Alternately, waste heat can be recovered simply by adding a waste heat recovery exchanger 124 without preheating the reflux. This is simpler in design and operation; however, less waste heat can be recovered.

Modifications to the operating conditions of this dual pressure system can be made for lower or higher average catalyst temperatures while still maintaining lower maximum temperatures in the system than is achievable with the prior art single operating pressure catalytic distillation hydrogenation system.

The invention claimed is:

1. A method of processing a cracked gas feed stream containing hydrogen, methane, ethylene, propylene and other $C_2$, $C_3$, $C_4$, $C_5$, $C_6$ and heavier unsaturated hydrocarbons to separate said ethylene and propylene from at least some of said other unsaturated hydrocarbons and to hydrogenate at least some of said other unsaturated hydrocarbons without hydrogenating ethylene and propylene comprising the steps of:

a. introducing said feed stream into a first column comprising a catalytic distillation hydrogenation column containing at least one catalyst bed and containing fractionation zones and operating at a first pressure and concurrently:

(i) selectively hydrogenating at least a portion of said other unsaturated hydrocarbons without hydrogenating said ethylene and propylene;

(ii) separating by fractional distillation the resulting hydrocarbon mixture into a first column gross overhead stream containing unreacted hydrogen, methane, ethylene, propylene and $C_4$ and $C_5$ compounds and a first bottoms stream containing primarily $C_6$ and heavier hydrocarbons and some $C_5$, $C_4$, $C_3$ and $C_2$ unsaturated hydrocarbons; and (iii) operating said first column so as to maintain said first bottoms stream at a temperature less than 200° C.;

b. separating said first column gross overhead stream into a first column net overhead stream and a first column reflux stream and introducing said first column reflux stream back into said first column;

c. introducing said first bottoms stream from said first column into a second column comprising a fractionation column operating at a second pressure lower than said first pressure and separating said first bottoms stream into a net bottoms stream containing $C_6$ and heavier hydrocarbons and a selected amount of $C_5$ hydrocarbons and into a second column gross overhead stream containing primarily additional $C_6$ and heavier hydrocarbons, and $C_5$, $C_4$, $C_3$ and $C_2$ hydrocarbons and operating said second column so as to maintain said net bottoms stream at a temperature less than 200° C.;

d. separating said second column gross overhead stream into a second column net overhead stream and a second column reflux stream and introducing said second column reflux stream back into said second column; and e. recycling said second column net overhead stream to said first column.

2. A method as recited in claim 1 wherein the temperature of said first bottoms stream and said net bottoms stream are less than 160° C.

3. A method as recited in claim 1 wherein said first and second columns are operated as depentanizers and said selected amount of $C_5$ hydrocarbons in said net bottoms stream from said second column is less than 1%.

4. A method as recited in claim 3 wherein said first column is operated at a pressure in the range of 14 to 20 kg/cm$^2$ and said second column is operated at a pressure in the range of 4 to 10 kg/cm$^2$.

5. A method as recited in claim 1 wherein said first and second columns are operated as debutanizers and said selected amount of $C_4$ hydrocarbons in said net bottoms stream is less than 1%.

6. A method as recited in claim 5 wherein said first column is operated at a pressure in the range of 28 to 43 kg/cm$^2$ and said second column is operated at a pressure in the range of 5 to 14 kg/cm$^2$.

7. A method as recited in claim 1 wherein the temperature of said catalyst beds is in the range of 90 to 135° C.

8. A method as recited in claim 1 wherein the step of recycling said second column net overhead stream comprises recycling below said catalyst bed.

9. A method as recited in claim 1 wherein the step of recycling said second column net overhead stream comprises recycling above said catalyst bed.

10. A method as recited in claim 8 and further including the step of preheating said second column net overhead before recycling to said first column by heat exchange with said second column gross overhead thereby cooling and partially condensing said second column gross overhead.

11. A method as recited in claim 10 wherein said preheated second column net overhead is further preheated by an external heat stream.

12. A method as recited in claim 9, wherein the step of recycling said second column net overhead stream further includes the step of cooling said second column net overhead stream.

13. A method as recited in claim 1 wherein said first column reflux stream is preheated by heat exchange with said first column gross overhead stream whereby a greater quantity of the heat contained in said first column gross overhead stream can be cooled to recover heat value before the gross overhead stream is finally cooled against ambient temperature cooling medium.

14. A method as recited in claim 1 wherein said cooled first column gross overhead stream is further cooled by ambient temperature cooling.

15. A method of processing a cracked gas feed stream containing hydrogen, methane, ethylene, propylene and other $C_2$, $C_3$, $C_4$, $C_5$ and $C_6$ and heavier hydrocarbons including unsaturated hydrocarbons to separate said ethylene and propylene from at least some of said other hydrocarbons and to hydrogenate at least some of said other unsaturated hydrocarbons without hydrogenating ethylene and propylene comprising the steps of:

a. introducing said feed stream into a catalytic distillation hydrogenation column operating at a first pressure and containing a hydrogenation catalyst and fractionation zones whereby at least a portion of said other unsaturated hydrocarbons are hydrogenated;

b. separating a net overhead stream containing ethylene, propylene and other $C_2$ to $C_4$ hydrocarbons and a selected amount of $C_5$ hydrocarbons;

c. separating a first bottoms stream containing said $C_6$ and heavier hydrocarbons and a portion of said $C_5$ and lighter hydrocarbons and maintaining said first bottoms stream at a temperature less than 200° C.;

d. introducing said first bottoms stream into a fractionation column operating at a second pressure lower than said first pressure;

e. separating a net bottoms stream containing said $C_6$ and heavier hydrocarbons and a selected portion of said $C_5$ hydrocarbons and maintaining said net bottoms stream at a temperature below 200° C.;

f. separating a fractionation column net overhead containing portions of said $C_6$ and heavier hydrocarbons and portions of said $C_5$ and lighter hydrocarbons; and g. recycling said fractionation column net overhead stream to said catalytic distillation hydrogenation column.

16. A method as recited in claim 15 wherein the temperature of said first bottoms stream and said net bottoms stream are less than 160° C.

17. A method as recited in claim 15 wherein said first and second columns are operated as depentanizers and said selected amount of $C_5$ hydrocarbons in said net bottoms stream from said second column is less than 1%.

18. A method as recited in claim 17 wherein said first column is operated at a pressure in the range of 14 to 20 kg/cm$^2$ and said second column is operated at a pressure in the range of 4 to 10 kg/cm$^2$.

19. A method as recited in claim 15 wherein said first and second columns are operated as debutanizers and said selected amount of $C_4$ hydrocarbons in said net bottoms stream is less than 1%.

20. A method as recited in claim 19 wherein said first column is operated at a pressure in the range of 28 to 43 kg/cm$^2$ and said second column is operated at a pressure in the range of 5 to 14 kg/cm$^2$.

21. A method as recited in claim 15 wherein the temperature of said catalyst beds is in the range of 90 to 135° C.

* * * * *